(12) United States Patent
Potadar et al.

(10) Patent No.: US 11,189,027 B2
(45) Date of Patent: Nov. 30, 2021

(54) METHOD AND SYSTEM FOR DETERMINING AREA TO BE SCANNED IN PERIPHERAL BLOOD SMEAR FOR ANALYSIS

(71) Applicant: SIGTUPLE TECHNOLOGIES PRIVATE LIMITED, Karnataka (IN)

(72) Inventors: Shreepad Potadar, Karnataka (IN); Dheeraj Mundhra, Kolkata (IN); Abhishek Shukla, New Delhi (IN); Raghu G, Telangana (IN); Amrutha Muralidharan, Kerala (IN); Deepak Kapoor, Uttar Pradesh (IN); Vijay Muralidharan, Chennai Tamil Nadu (IN); Nivedita Muthusubramanian, Nadu (IN); Bharath Cheluvaraju, Karnataka (IN); Apurv Anand, Karnataka (IN); Tathagato Rai Dastidar, Karnataka (IN); Rohit Kumar Pandey, Karnataka (IN)

(73) Assignee: Sigtuple Technologies Private Limited, Karnataka (IN)

( * ) Notice: Subject to any disclaimer, the term of this patent is extended or adjusted under 35 U.S.C. 154(b) by 32 days.

(21) Appl. No.: 16/622,110

(22) PCT Filed: May 15, 2018

(86) PCT No.: PCT/IB2018/053388
§ 371 (c)(1),
(2) Date: Dec. 12, 2019

(87) PCT Pub. No.: WO2018/211418
PCT Pub. Date: Nov. 22, 2018

(65) Prior Publication Data
US 2020/0242757 A1     Jul. 30, 2020

(30) Foreign Application Priority Data

May 15, 2017 (IN) .............................. 201741014502

(51) Int. Cl.
*G06T 7/00* (2017.01)
*G06T 7/73* (2017.01)
(Continued)

(52) U.S. Cl.
CPC .............. *G06T 7/0012* (2013.01); *C12Q 1/06* (2013.01); *G01N 1/2813* (2013.01); *G01N 33/80* (2013.01);
(Continued)

(58) Field of Classification Search
None
See application file for complete search history.

(56) References Cited

U.S. PATENT DOCUMENTS

| 4,453,266 A * | 6/1984 | Bacus ...................... G06T 7/64 356/39 |
| 8,345,227 B2 * | 1/2013 | Zahniser ............ G01N 15/1475 356/40 |

(Continued)

FOREIGN PATENT DOCUMENTS

| JP | 2002281347 A * | 9/2002 | ............... G06T 5/00 |
| WO | WO-2013158506 A2 * | 10/2013 | ......... G01N 21/8483 |

OTHER PUBLICATIONS

Stanbrough, J. (Jul. 17, 2015). The center of mass. Retrieved Mar. 22, 2021, from http://www.batesville.k12.in.us/physics/apphynet/dynamics/center%20of%20mass/Center_of_Mass_1.html (Year: 2015).*

(Continued)

*Primary Examiner* — Vu Le
*Assistant Examiner* — Courtney Joan Nelson
(74) *Attorney, Agent, or Firm* — Foley & Lardner LLP

(57) ABSTRACT

Disclosed subject matter relates to Peripheral Blood Smear (PBS) that determines an area to be scanned in PBS for
(Continued)

analysis. A PBS analysing system captures a focused image at each of plurality of positions in the PBS and determines Quality Indicators (QIs) in focused image. Further, a region is identified in PBS where QIs of focused image satisfy predefined QI threshold limits, as a monolayer region of PBS and determines an initiation point in monolayer region based on cell count value and co-ordinates of each of the plurality of positions located in the monolayer region. Finally, the area to be scanned in monolayer region is determined based on the initiation point and a predefined scan pattern. Determining the area to be scanned yields accurate and faster results.

26 Claims, 9 Drawing Sheets

(51) Int. Cl.
*C12Q 1/06* (2006.01)
*G01N 1/28* (2006.01)
*G01N 33/80* (2006.01)
*G01N 35/00* (2006.01)
*G06K 9/00* (2006.01)

(52) U.S. Cl.
CPC ..... *G01N 35/00029* (2013.01); *G06K 9/0014* (2013.01); *G06T 7/73* (2017.01); *G06T 2207/30024* (2013.01)

(56) References Cited

U.S. PATENT DOCUMENTS

| | | | |
|---|---|---|---|
| 2004/0109608 A1 | 6/2004 | Love et al. | |
| 2004/0217270 A1* | 11/2004 | Publicover | G01Q 10/06 250/234 |
| 2007/0076190 A1* | 4/2007 | Nakaya | G01N 15/1475 356/39 |
| 2014/0356938 A1* | 12/2014 | Kendall | G01N 21/27 435/288.7 |

OTHER PUBLICATIONS

Machine translation of JP-2002281347-A (Year: 2002).*
International Search Report & Written Opinion for PCT/IB2018/053388 dated Aug. 9, 2018, pp. 1-9.

* cited by examiner

METHOD AND SYSTEM FOR DETERMINING AREA TO BE SCANNED IN PERIPHERAL BLOOD SMEAR FOR ANALYSIS

CROSS-REFERENCE TO RELATED APPLICATIONS

This application is the U.S. national stage of PCT Application No. PCT/IB2018/053388, filed May 15, 2018, which claims priority to and the benefit of Indian Application No. 201741014502, filed May 15, 2017, the contents of which are incorporated herein by reference in their entireties.

The following specification particularly describes the invention and the manner in which it is to be performed.

TECHNICAL FIELD

The present subject matter relates generally to a Peripheral Blood Smear (PBS), and more particularly, but not exclusively to a method and a system for determining an area to be scanned in the PBS for analysis.

BACKGROUND

Generally, Peripheral Blood Smear (PBS) is considered to be a golden standard for detecting several haematological disorders. Analysis of PBS helps in providing a count of different types of cells such as Red Blood Cells (RBCs), White Blood Cells (WBCs), platelets and the like. Also, the analysis of PBS helps in observing morphological abnormalities of the cells. However, an entire area of PBS would not be appropriate for accurately analyzing the cells. Therefore, detecting an area in the PBS that provides a clear visualization of the cells for analysis is of utmost importance.

Former techniques involve manually locating the desirable area in the PBS for analysis. However, manually locating the desirable area in the PBS is a laborious task and also error prone. Therefore, next set of techniques focused on automating the process of locating the desirable area and scanning the cells in the desirable area, with a vision of enhancing reproducibility of results and reducing cost involved in analysis. The existing systems capture images of the PBS and analyze the images to perform automated analysis. However, systems implementing the existing techniques are very limited due to high cost of adoption, thereby negatively affecting availability of the systems for analysis.

Further, the existing techniques perform a two stage scanning process for obtaining the images of the cells from the desired area in the PBS. First stage may comprise utilizing a low magnification lens to locate the objects of interest in the PBS and the second stage may include thorough scanning of the identified locations in the PBS using a high magnification lens. The two stage scanning process for locating and analyzing the cells in the PBS is extremely time consuming, thereby increasing Turn Around Time (TAT) of analysis. Also, some of the existing techniques perform oil immersion based scanning (i.e. slides are prepared with oil immersion techniques to achieve best refraction under high magnification). However, oil immersion adds an extra tedious task to automated scanning process that increases the TAT and also may lead to inaccurate results or damage of lens, if not maintained properly.

Furthermore, the existing techniques are applicable for automatically generated PBS and may not work with manually prepared PBS.

The information disclosed in this background of the disclosure section is only for enhancement of understanding of the general background of the disclosure and should not be taken as an acknowledgement or any form of suggestion that this information forms prior art already known to a person skilled in the art

SUMMARY

One or more shortcomings of the prior art may be overcome, and additional advantages may be provided through the present disclosure. Additional features and advantages may be realized through the techniques of the present disclosure. Other embodiments and aspects of the disclosure are described in detail herein and are considered a part of the claimed disclosure.

Disclosed herein is a method for determining an area to be scanned in a Peripheral Blood Smear (PBS) for analysis. The method includes capturing, by a PBS analyzing system, a focused image at each of a plurality of positions in the PBS. Further, the PBS analyzing system determines Quality Indicators (QIs) in the focused image. The QIs comprise a cell count value, a normalized sharpness value and an average intensity value. Upon determining the QIs, the PBS analyzing system identifies a region in the PBS where the QIs of the focused image satisfy predefined QI threshold limits, as a monolayer region of the PBS. Further, the PBS analyzing system determines an initiation point in the monolayer region based on the cell count value determined in the focused image captured at each of the plurality of positions located in the monolayer region and co-ordinates of each of the plurality of positions located in the monolayer region. Finally, the PBS analyzing system determines the area to be scanned in the monolayer region based on the initiation point and a predefined scan pattern selected for scanning the area.

Further, the present disclosure includes a Peripheral Blood Smear (PBS) analyzing system for determining an area to be scanned in a PBS for analysis. The PBS analyzing system includes a processor and a memory communicatively coupled to the processor. The memory stores the processor-executable instructions, which, on execution, causes the processor to capture a focused image at each of plurality of positions in the PBS. Further, the processor determines Quality Indicators (QIs) in the focused image. The QIs comprise a cell count value, a normalized sharpness value and an average intensity value. Upon determining the QIs, the processor identifies a region in the PBS where the QIs of the focused image satisfy predefined QI threshold limits, as a monolayer region of the PBS. Further, the processor determines an initiation point in the monolayer region based on the cell count value determined in the focused image captured at each of the plurality of positions located in the monolayer region and co-ordinates of each of the plurality of positions located in the monolayer region. Finally, the processor determines the area to be scanned in the monolayer region based on the initiation point and a predefined scan pattern selected for scanning the area.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE ACCOMPANYING DIAGRAMS

The accompanying drawings, which are incorporated in and constitute a part of this disclosure, illustrate exemplary embodiments and, together with the description, serve to explain the disclosed principles. In the figures, the left-most digit(s) of a reference number identifies the figure in which the reference number first appears. The same numbers are used throughout the figures to reference like features and components. Some embodiments of system and/or methods in accordance with embodiments of the present subject matter are now described, by way of example only, and with reference to the accompanying figures, in which:

Figure 1A:
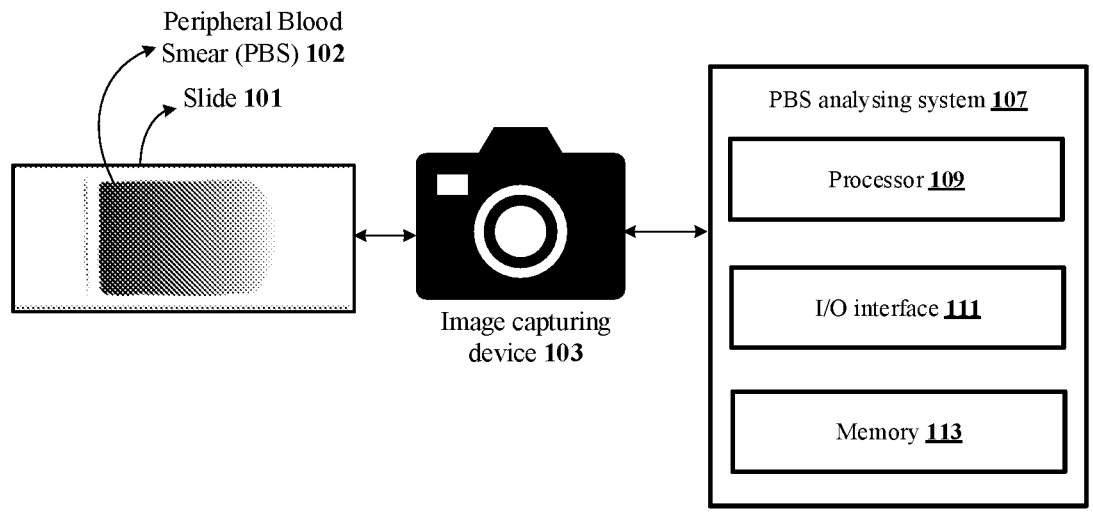
FIG. 1A shows an exemplary architecture for determining an area to be scanned in a Peripheral Blood Smear (PBS) for analysis in accordance with some embodiments of the present disclosure.
Figure 1B:
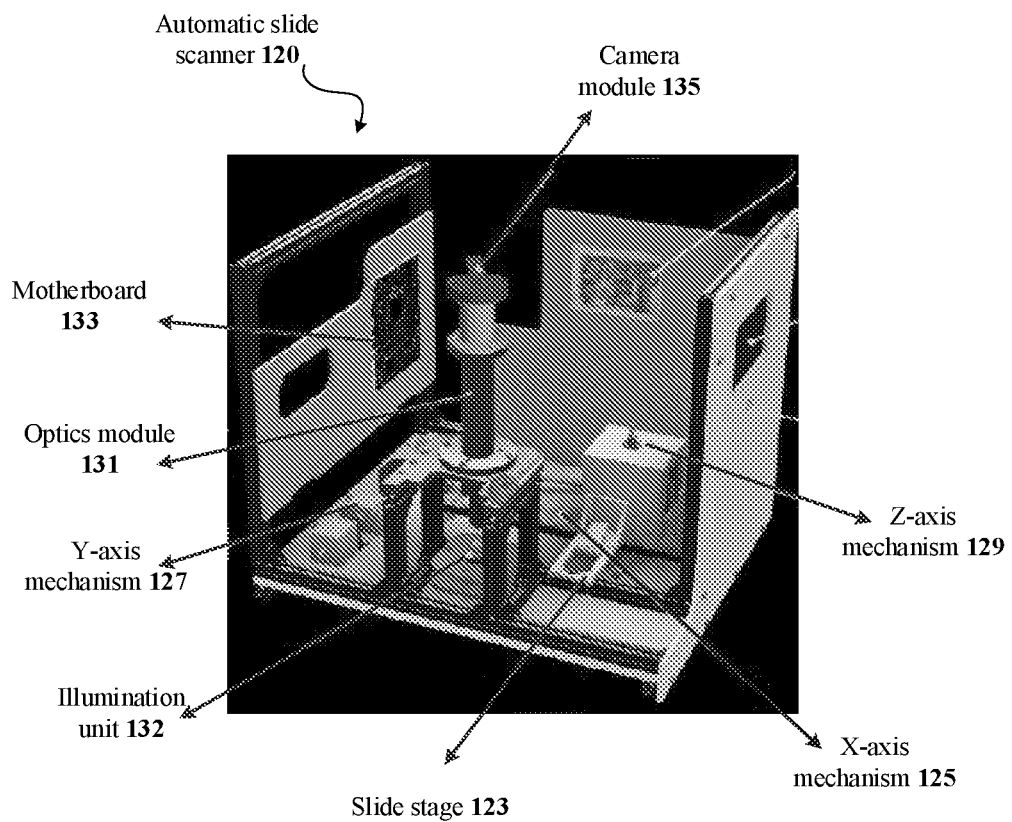
FIG. 1B shows an exemplary automatic slide scanner in accordance with some embodiments of the present disclosure.
Figure 1C:
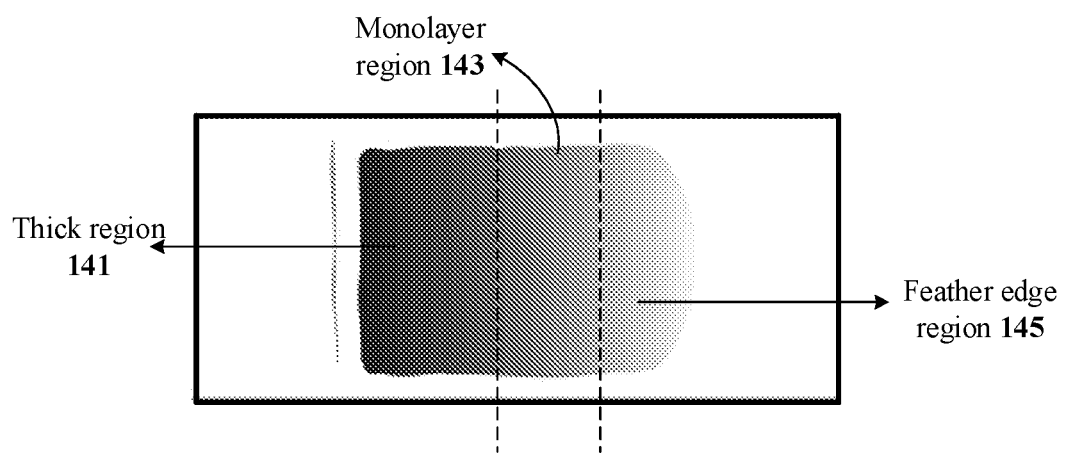
FIG. 1C (a) shows different regions of a Peripheral Blood Smear (PBS) in accordance with some embodiments of the present disclosure.
Figure 1C:
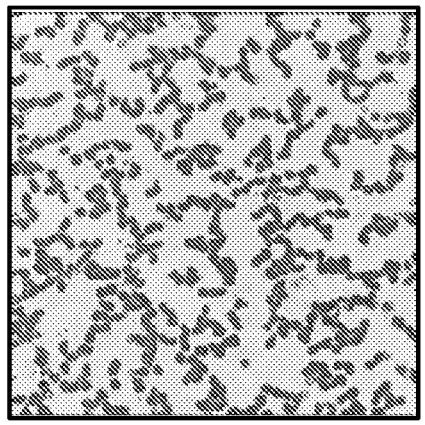
Figure 1C:
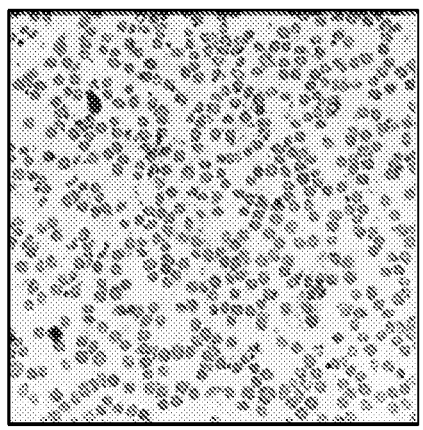
Figure 1C:
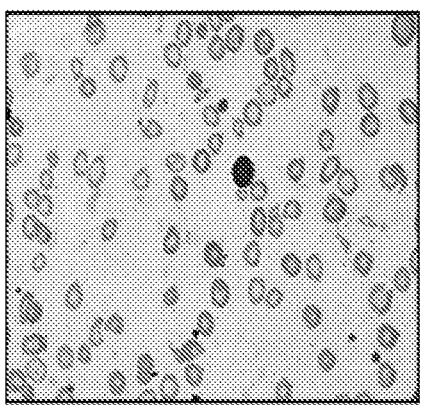
Figure 2A:
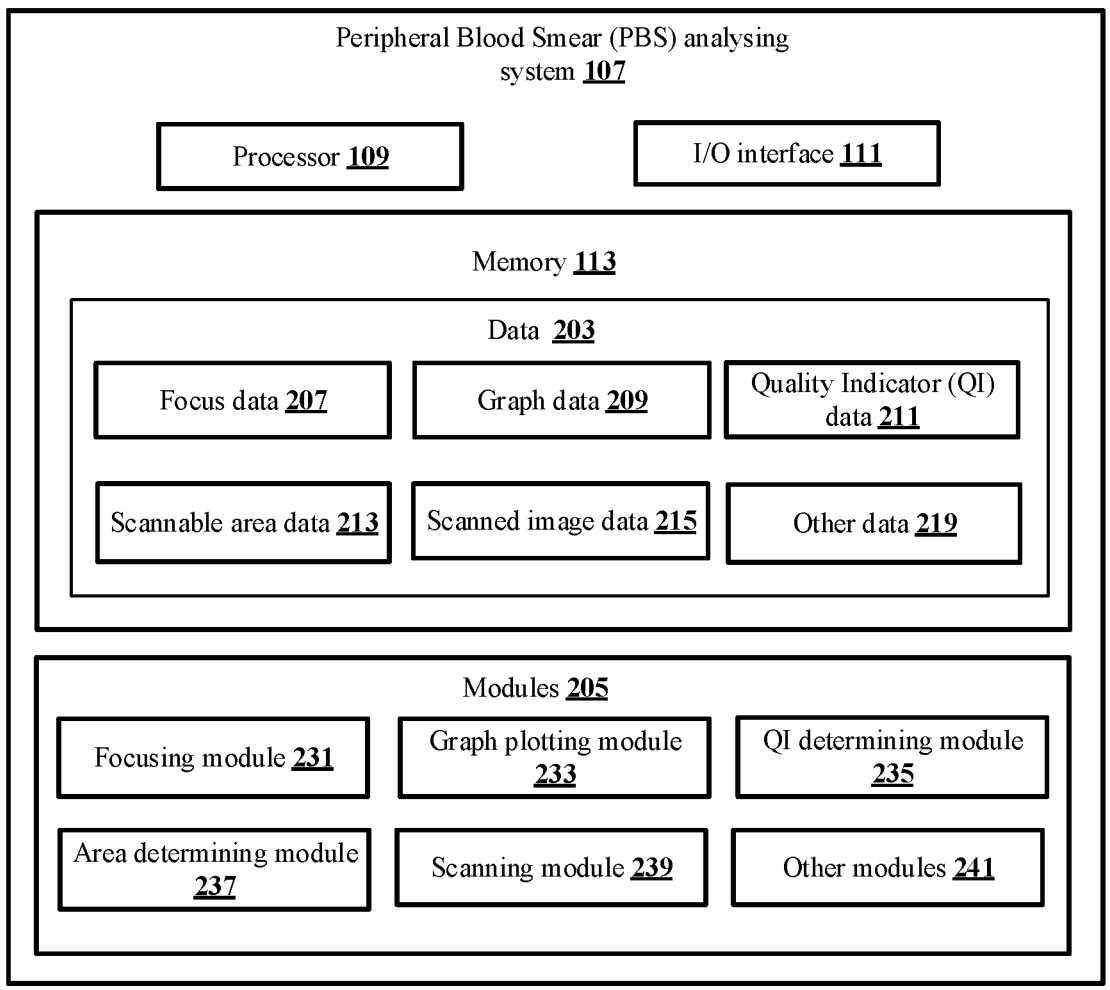
Figure 2B:
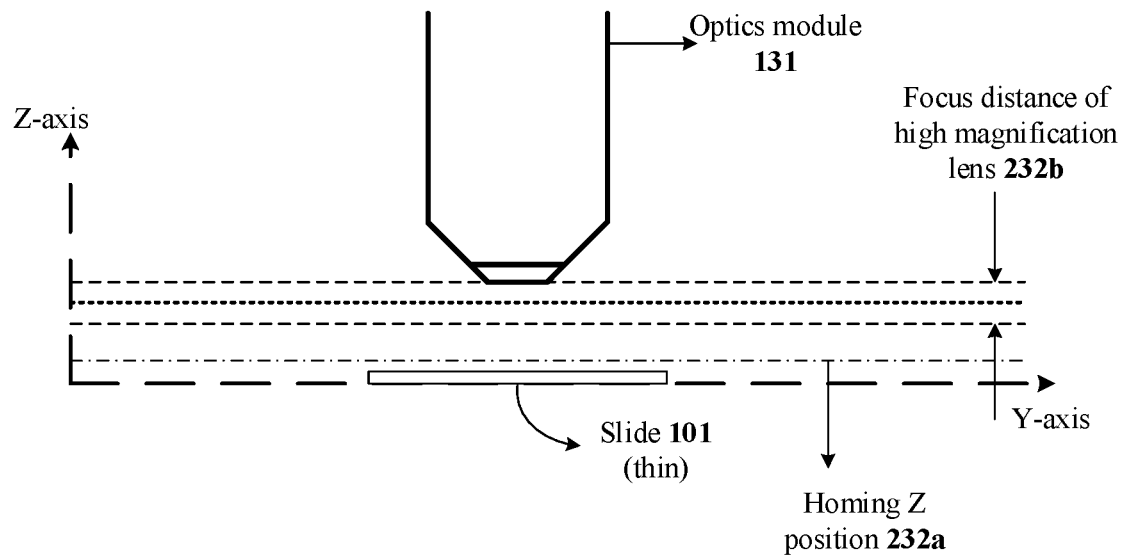
Figure 2B:
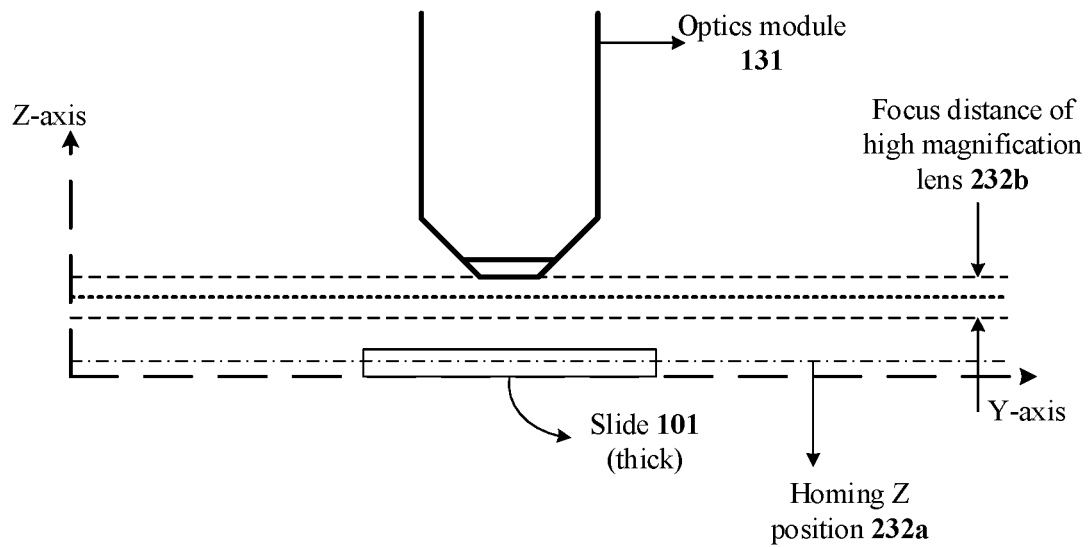
Figure 2C:
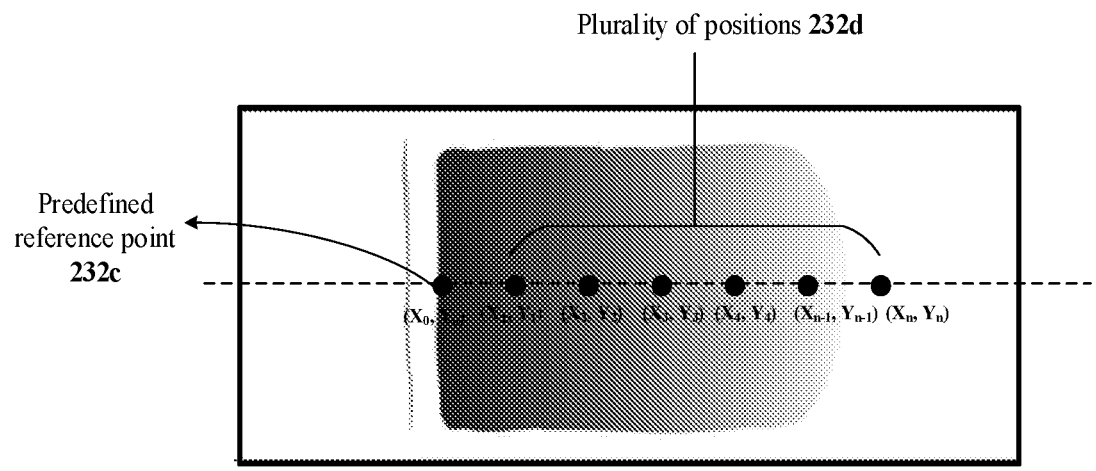
Figure 2D:
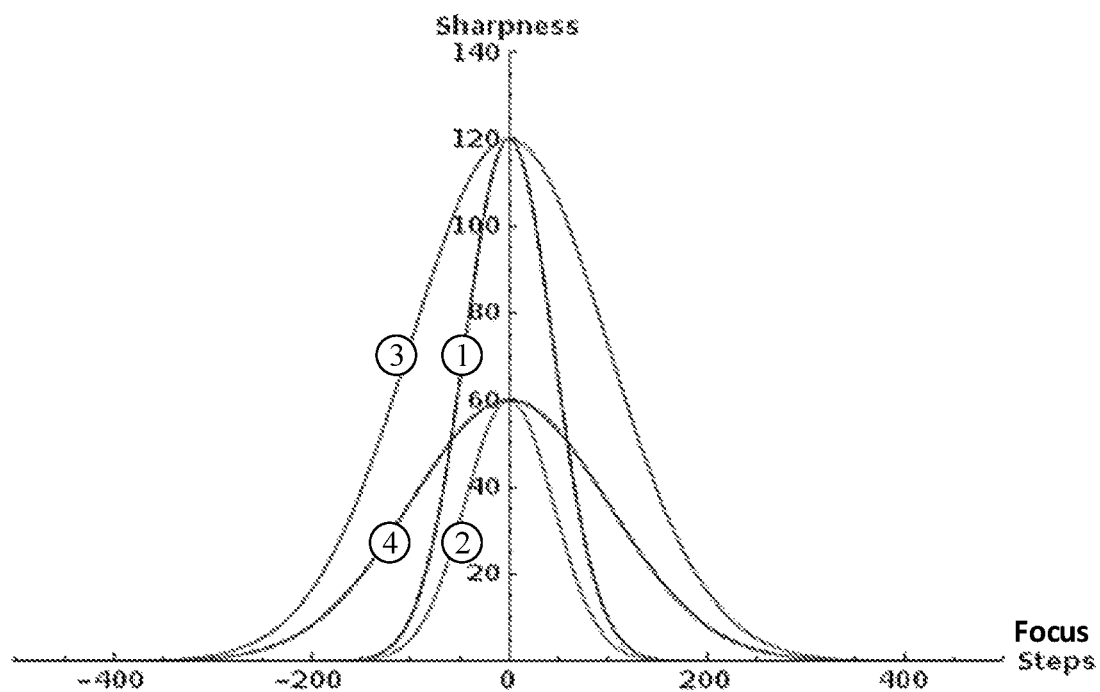
Figure 2E:
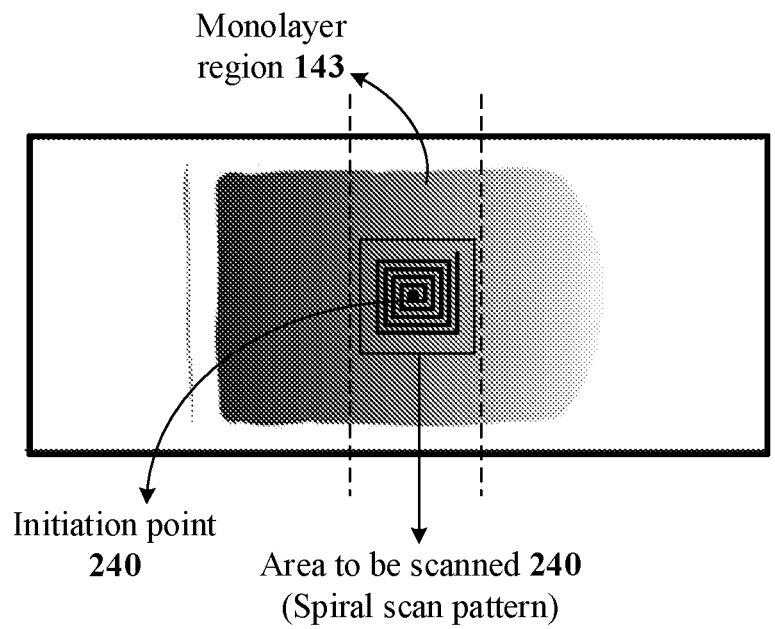
Figure 2E:
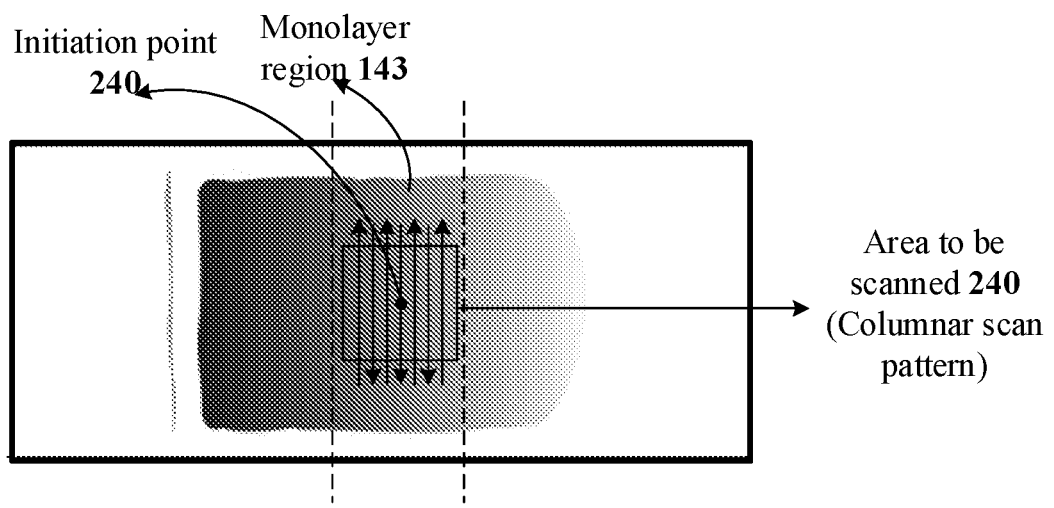
Figure 3:
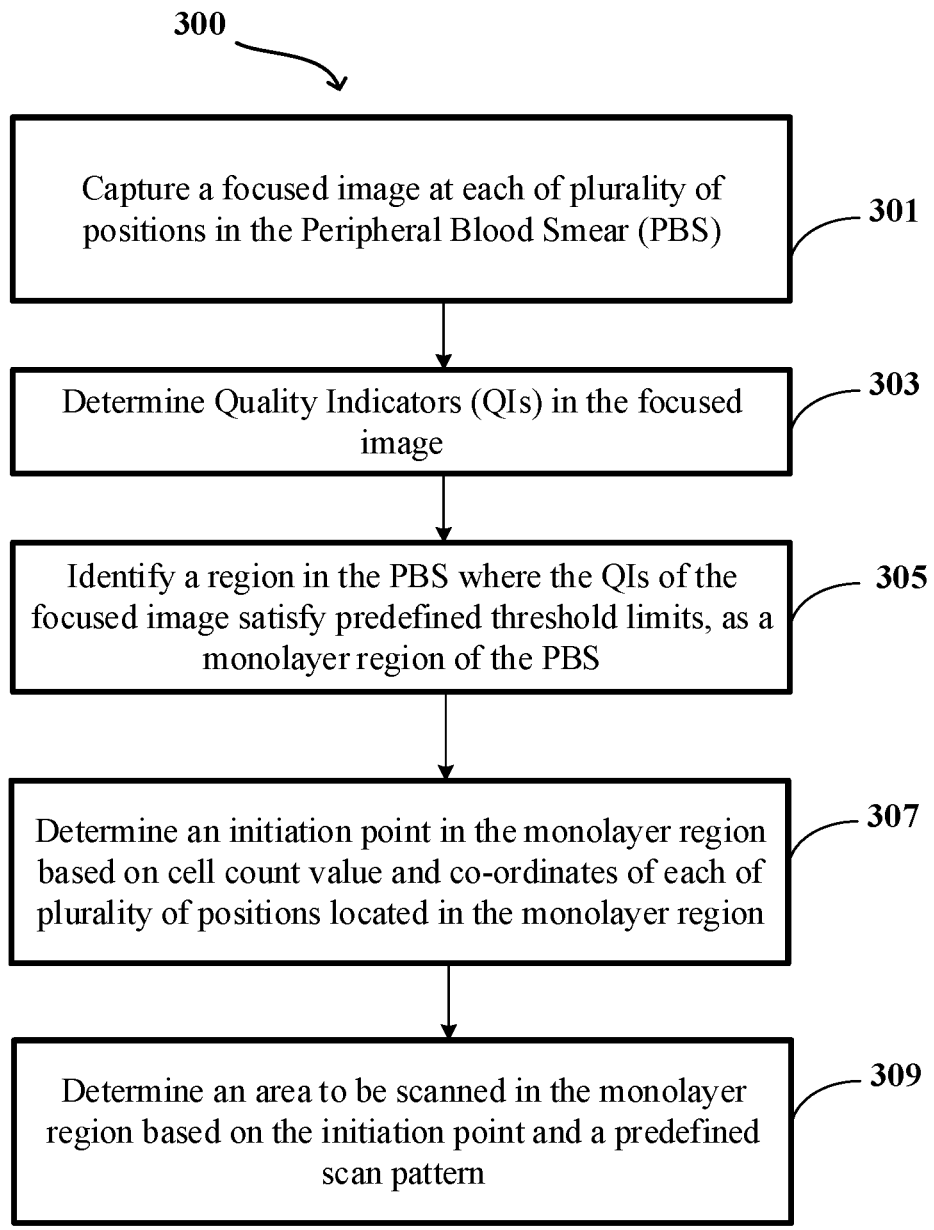
Figure 4:
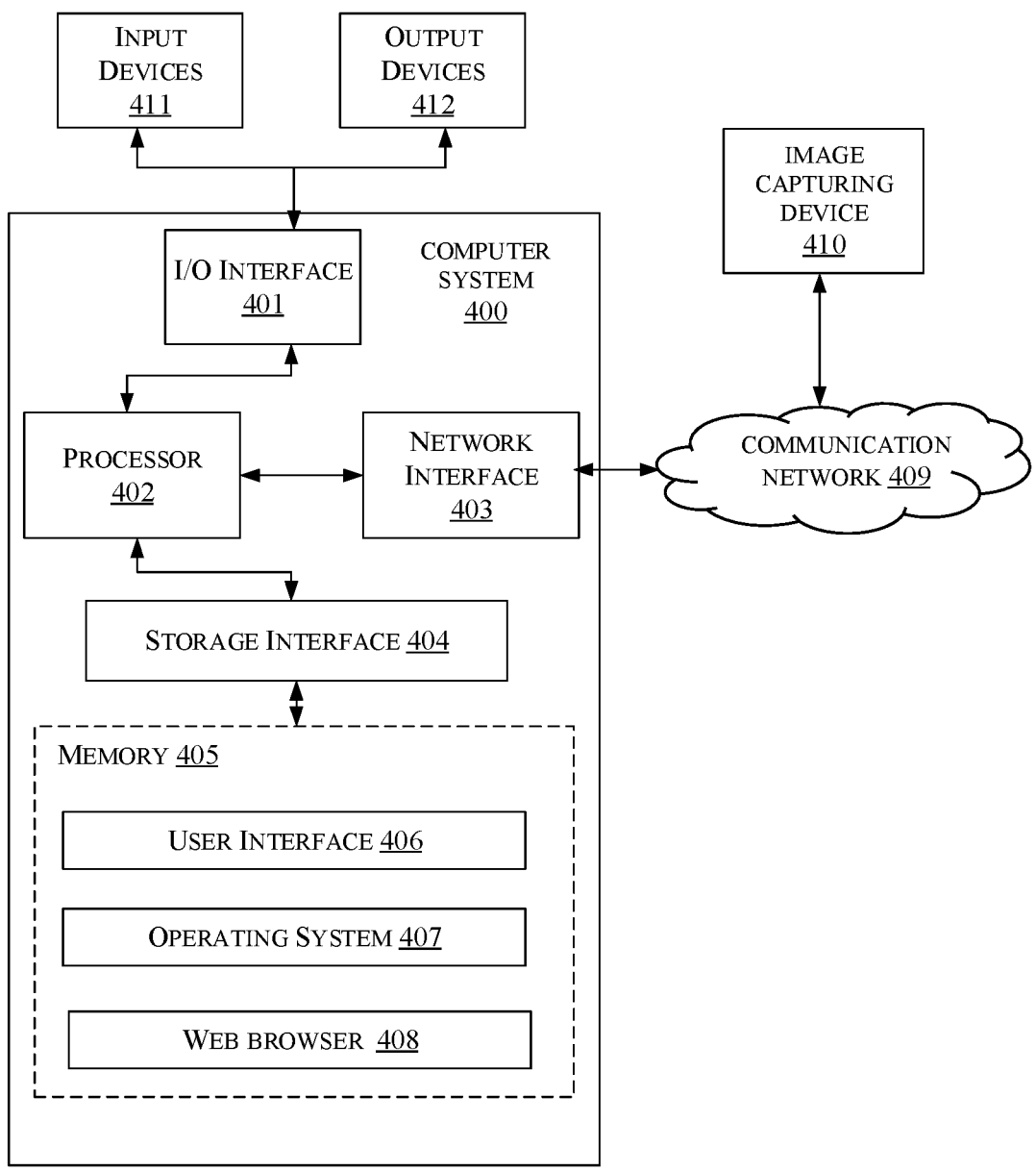

FIG. 1C (b)-FIG. 1C (d) show overlapping distribution of blood cells, non-overlapping distribution of blood cells and sparsely separated distribution of blood cells in a thick region, a monolayer region and a feather edge region respectively, of a Peripheral Blood Smear (PBS) in accordance with some embodiments of the present disclosure;

FIG. 2A shows a detailed block diagram of a Peripheral Blood Smear (PBS) analyzing system for determining an area to be scanned in a PBS for analysis in accordance with some embodiments of the present disclosure;

FIG. 2B (a) and FIG. 2B (b) show exemplary homing Z position for varying thickness of slides in accordance with some embodiments of the present disclosure;

FIG. 2C show an exemplary embodiment indicating a predefined reference point in accordance with some embodiments of the present disclosure;

FIG. 2D shows an exemplary bell-curve graph in accordance with some embodiments of the present disclosure;

FIG. 2E (a) and FIG. 2E (b) show exemplary scan patterns in accordance with some embodiments of the present disclosure;

FIG. 3 shows a flowchart illustrating a method for determining an area to be scanned in a Peripheral Blood Smear (PBS) for analysis in accordance with some embodiments of the present disclosure; and FIG. 4 is a block diagram of an exemplary computer system for implementing embodiments consistent with the present disclosure.

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and executed by a computer or processor, whether or not such computer or processor is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the forms disclosed, but on the contrary, the disclosure is to cover all modifications, equivalents, and alternative falling within the scope of the disclosure.

The terms "comprises", "comprising", "includes" or any other variations thereof, are intended to cover a non-exclusive inclusion, such that a setup, device or method that includes a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or method.

Disclosed herein are a method and a system for determining an area to be scanned in a Peripheral Blood Smear (PBS) for analysis. A PBS analyzing system initially comprises a calibration phase to determine the area to be scanned in the PBS. Upon determining the area to be scanned, the PBS analyzing system comprises a scanning phase to scan the area. In some embodiments, in the calibration phase, the PBS analyzing system may capture a focused image at each of plurality of positions in the PBS. In some embodiments, the PBS analyzing system may capture the focused image using an image capturing device associated with the PBS analyzing system. Further, the PBS analyzing system may determine Quality Indicators (QIs) in the focused image. As an example, the QIs may include, but not limited to, a cell count value, a normalized sharpness value, an average intensity value, a sharpness value, a density value and Red Blood Cells (RBC) count ratio. Upon determining the QIs, the PBS analyzing system may identify a region in the PBS where the QIs of the focused image satisfy predefined QI threshold limits, as a monolayer region of the PBS. Finally, the PBS analyzing system may determine an initiation point in the monolayer region. In some embodiments, the initiation point may be determined based on the cell count value determined in the focused image captured at each of the plurality of positions located in the monolayer region and co-ordinates of each of the plurality of positions located in the monolayer region. Upon determining the initiation point, the PBS analyzing system may determine the area to be scanned based on the initiation point and a predefined scan pattern. Upon determining the area to be scanned, the PBS analyzing system may scan the area in the predefined scan pattern around the initiation point. In some embodiments, the PBS analyzing system may scan the area until at least one of, exhaustion of the area or desired number of Field Of Views (FOVs) in the area that satisfy analysis criteria of the PBS are attained. In some embodiments, the analysis criteria may be application specific. As an example, if the application demands a Complete Blood Count (CBC) report, then the analysis criteria may be obtaining CBC.

In the present disclosure, determining the area to be scanned within the monolayer region of the PBS, yields accurate and fast results during analysis. Also, scanning the determined area from the initiation point may enable achieving accurate and fast results in less than 120 FOVs. Further, the present disclosure discloses a feature wherein a single high magnification lens is used to identify the area to be scanned and for further scanning the area, thereby reducing enormous amount of time that is spent by the existing techniques in performing a two stage scanning process using two different magnification lenses.

A description of an embodiment with several components in communication with each other does not imply that all such components are required. On the contrary a variety of optional components are described to illustrate the wide variety of possible embodiments of the disclosure.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

FIG. 1A shows an exemplary architecture for determining an area to be scanned in a Peripheral Blood Smear (PBS) for analysis in accordance with some embodiments of the present disclosure.

The architecture 100 includes a slide 101, an image capturing device 103 and a Peripheral Blood Smear (PBS) analyzing system 107. In some embodiments, standard size of the slide 101 may be 25 mm×75 mm with minor variations. In some other embodiments, the present disclosure works with slides of variable thickness. Further, the image capturing device 103 may be associated with the PBS analyzing system 107 to capture images of object of interest on the slide 101. As an example, the image capturing device 103 may be a camera, a smart phone, a tablet and the like. Further, the PBS analyzing system 107 may be configured in an automatic slide scanner 120 as shown in the FIG. 1B. In some embodiments, the PBS analyzing system 107 may be associated with the automatic slide scanner 120 via a communication network (not shown in the FIG. 1A). As an example, the communication network may be a wired communication network or a wireless communication network.

The automatic slide scanner 120 may include, but not limited to, a slide stage 123, X-axis mechanism 125, Y-axis mechanism 127, a Z-axis mechanism 129, an optics module 131, an illumination unit 132, a motherboard 133 and a camera module 135. The slide stage 123 is a component of the automatic slide scanner 120 that provides a surface for placing the slide 101 to be examined. Further, the X-axis mechanism 125 may enable movement of the slide stage 123 along X-axis, the Y-axis mechanism 127 may enable movement of the slide stage 123 along Y-axis and the Z-axis mechanism 129 may enable movement of the slide stage 123 along Z-axis. The optics module 131 may include an eyepiece and a high magnification lens configured to focus on the slide 101 placed on the slide stage 123. In the present disclosure, the optics module 131 may be in a fixed position, however, the slide stage 123 may move along X-axis, Y-axis and Z-axis, thereby enabling the optics module 131 to focus any desired part of the slide 101 placed on the slide stage 123. Further, the illumination unit 132 may be configured below the optics module 131 as shown in the FIG. 1B, to illuminate the slide 101 to be examined. Furthermore, the camera module 135 may include, but not limited to, the image capturing device 105 to capture images of the objects of interest on the slide 101. Further, the PBS analyzing system 107 may be configured in the motherboard 133 of the automatic slide scanner 120.

Referring back to FIG. 1A, further, surface of the slide 101 may comprise the PBS 102. In some embodiments, the PBS 102 may be an automatically generated PBS 102 using automatic smearers. In some other embodiments, the PBS 102 may be created manually based on standard operating procedures of laboratories. In some embodiments, the PBS 102 may be typically a tongue shaped smear that includes a thick region 141, a monolayer region 143 and a feather edge region 145. The thick region 141 may be present at start of the smear as shown in the FIG. 1C (a). In the thick region 141, blood cells may be clumped together as shown in FIG. 1C (b). Typically, the thick region 141 extends for at least two third or more of the entire length of the PBS 102. Analysis of morphology of individual blood cells is nearly impossible in the thick region 141. Therefore, the thick region 141 may not be a desired region of the PBS 102 for performing analysis.

In some embodiments, the monolayer region 143 is a region of the PBS 102 where the blood cells are either well separated or barely in contact with one another. The monolayer region 143 may start at the end of the thick region 141 as shown in the FIG. 1C (a). Since the blood cells are non-overlapping in the monolayer region 143 as shown in FIG. 1C (c), this region may be the desired region of the PBS 102 for performing analysis.

In some embodiments, the feathered edge region 145 is a region of the PBS 102 that lies at end of the PBS 102 as shown in the FIG. 1C (a). The blood cells are highly separated in the feathered edge region 145 as shown in FIG. 1C (d). Also, the blood cells in the feathered edge region 145 may lose their natural morphological characteristics, due to applied pressure while creating the PBS 102, thereby making this region unsuitable for analysis.

Further, the PBS analyzing system 107 may include a processor 109, an Input/Output (I/O) interface 111 and a memory 113. The I/O interface 111 may be configured to receive images captured by the image capturing device 103. The images received from the image capturing device may be stored in the memory 113. In some embodiments, the processor 109 may initially mark plurality of positions starting from a predefined reference point, till end of the PBS 102. As an example, the predefined reference point may be a centre point along the shorter edge of the slide 101. In some embodiments, the processor 109 may separate each of the plurality of positions by a predefined distance till the end of the PBS 102. Further, the processor 109 may capture a focused image at each of plurality of positions in the PBS 102, using the image capturing device 105. In some embodiments, the focused image is an image corresponding to sharpest focus attainable at the corresponding position. In some embodiments, the processor 109 may capture the focused image using a predefined focusing technique. As an example, the predefined focusing technique may be a full z-stack focusing technique.

Further, the processor 109 may determine Quality Indicators (QIs) in the focused image captured at each of the plurality of positions. In some embodiments, the QIs may include, but not limited to, a cell count value, a normalized sharpness value and an average intensity value, a sharpness value, a density value and Red Blood Cells (RBC) count ratio. Upon determining the QIs in the focused image captured at each of the plurality of positions, the processor 109 may compare the QIs with predefined QI threshold limits. The processor 109 may identify a region of the PBS 102 where the QIs of the focused image satisfied the predefined QI threshold limits as the monolayer region 143 of the PBS 102. Further, the processor 109 may determine an initiation point in the monolayer region 143 based on the cell count value determined in the focused image captured at each of the plurality of positions located in the monolayer region 143 and co-ordinates of each of the plurality of positions located in the monolayer region 143. Upon determining the initiation point, the processor 109 may determine the area to be scanned based on the initiation point and a predefined scan pattern. As an example, the predefined scan pattern may include, but not limited to, a spiral scan pattern and a columnar scan pattern.

Upon determining the area to be scanned, the processor 109 may scan the area in the predefined scan pattern around the initiation point. In some embodiments, the initiation point may mark a starting position of the scanning process. In some embodiments, the processor 109 may scan the area until at least one of, exhaustion of the area or desired number of Field Of Views (FOVs) in the area that satisfy analysis criteria of the PBS 102 are attained.

FIG. 2A shows a detailed block diagram of a Peripheral Blood Smear (PBS) analyzing system for determining an area to be scanned in a PBS 102 for analysis in accordance with some embodiments of the present disclosure.

In some implementations, the PBS analyzing system 107 may include data 203 and modules 205. As an example, the data 203 is stored in a memory 113 configured in the PBS analyzing system 107 as shown in the FIG. 2A. In some embodiments, the data 203 may include focus data 207, graph data 209, Quality Indicator (QI) data 211, scannable area data 213, scanned image data 215 and other data 219. In the illustrated FIG. 2A, modules 205 are described herein in detail.

In some embodiments, the data 203 may be stored in the memory 113 in form of various data structures. Additionally, the data 203 can be organized using data models, such as relational or hierarchical data models. The other data 219 may store data, including temporary data and temporary files, generated by the modules 205 for performing the various functions of the PBS analyzing system 107.

In some embodiments, the data 203 stored in the memory 113 may be processed by the modules 205 of the PBS analyzing system 107. The modules 205 may be stored within the memory 113. In an example, the modules 205 communicatively coupled to the processor 109 configured in the PBS analyzing system 107, may also be present outside the memory 113 as shown in FIG. 2A and implemented as hardware. As used herein, the term modules 205 may refer to an application specific integrated circuit (ASIC), an electronic circuit, a processor (shared, dedicated, or group) and memory that execute one or more software or firmware programs, a combinational logic circuit, and/or other suitable components that provide the described functionality.

In some embodiments, the modules 205 may include, for example, a focusing module 231, a graph plotting module 233, a QI determining module 235, an area determining module 237, a scanning module 239 and other modules 241. The other modules 241 may be used to perform various miscellaneous functionalities of the PBS analyzing system 107. It will be appreciated that such aforementioned modules 205 may be represented as a single module or a combination of different modules.

In some embodiments, the focusing module 231 may capture a focused image of a PBS 102 contained on a slide 101, using an image capturing device 103 associated with the PBS analyzing system 107. In some embodiments, the PBS 102 may be either automatically generated PBS 102 using automatic smearers or a manually created PBS 102 using standard operating procedures of laboratories. Initially, the focusing module 231 may move a slide stage 123 holding the slide 101 to a homing Z position 232a as shown in the FIG. 2B (a). In some embodiments, the homing Z position 232a may be a position below a focus distance of the high magnification lens 232b, such that slides 101 of thickness ranging from 0.8 mm to 1.2 mm may have their respective top surfaces at least 1 mm away from the high magnification lens as shown in the FIG. 2B (a) and FIG. 2B (b). Further, the focusing module 231 may mark plurality of positions starting from a predefined reference point, till end of the PBS 102. An exemplary predefined reference point 232c and exemplary plurality of positions 232d are as shown in the FIG. 2C. As an example, the predefined reference point may be a centre point along shorter edge of the slide 101. In some embodiments, the focusing module 231 may separate each of the plurality of positions by a predefined distance till the end of the PBS 102.

Further, at each of the plurality of positions, the focusing module 231 may capture the focused image of the PBS 102 using a predefined focusing technique. As an example, the predefined focusing technique may be a full z-stack focusing technique. In some embodiments, to capture the focused image, the focusing module 231 may initially move the slide stage 123, from the homing Z position, along a Z-axis by selecting focus steps (i.e. varying height of the slide stage 123 by selecting the focus steps). In some embodiments, the focus step is a distance covered by the slide stage 123 (i.e. increase in height of the slide stage 123 from the homing Z position). Each focus step may cover minimum distance or short distance such that, the focusing module 231 does not miss sharpest focus corresponding to each of the plurality of positions. With each focus step, the slide stage 123 moves upwards along Z-axis, thereby increasing sharpness value at each focus step. As the slide stage 123 moves upwards, at one focus step, the sharpness value may drop to a value lower than the sharpness value at previous focus step. The focusing module 231 may identify the previous focus step as the focus step corresponding to sharpest focus (i.e. the focus step corresponding to highest sharpness value for the corresponding position). Further, the focusing module 231 may move the slide stage 123 backward to the focus step corresponding to the sharpest focus and capture the focused image. The focused image and the focus step corresponding to the sharpest focus for each of the plurality of positions may be stored as the focus data 207.

In some embodiments, the graph plotting module 233 may plot a bell-curve graph indicating the focus steps taken for each of the plurality of positions and the corresponding sharpness value at each focus step of the plurality of positions, when the focused image is captured. An exemplary bell-curve graph is as shown in the FIG. 2D. X-axis of the bell-curve graph indicates focus steps, whereas Y-axis of the bell-curve graph indicates sharpness values. In some embodiments, width and height of a bell-curve depend on nature of Field Of View (FOV). In some embodiments, a well stained PBS 102, where blood cells are opaque and starkly differentiated from background, typically have a broader bell-curve. Bell-curves 3 and 4 of the FIG. 2D can be construed as belonging to well stained PBS 102. On the contrary, a lightly stained PBS 102, where the blood cells are translucent, typically have a narrow bell-curve. Bell-curves 1 and 2 of the FIG. 2D can be construed as belonging to lightly stained PBS 102. In some embodiments, the bell-curve graph may be stored as graph data 209.

Further, the Quality Indicator (QI) determining module 235 may determine QIs in the focused image captured at each of the plurality of positions. In some embodiments, the QIs may include, but not limited to, a cell count value, a normalized sharpness value and an average intensity value, a sharpness value, a density value and Red Blood Cells (RBC) count ratio as illustrated below. The QIs determined for each focused image may be stored as the QI data 211.

Sharpness value: Sharpness value may be defined as magnitude of gradients in the FOV. The QI determining module 235 may determine the sharpness value by computing an L2-norm of an image after applying a Sobel operator on a green channel of the image. Typically, a blur image may be considered to have a lower sharpness value, while a focused image may be considered to have a larger sharpness value. In some embodiments, absolute value of sharpness may not depend only on degree of focus, but also on the number of objects present in the image. Therefore, two equally focused images may have different sharpness values.

Predefined QI threshold limit: Since a low sharpness value indicates a blurred image, or an image with very few visible blood cells, a lower limit may be defined for the sharpness value to accept an image as belonging to a monolayer region 143.

Average Intensity value: The QI determining module 235 may compute an average pixel value of the green channel for every image. An empty area (i.e. region comprising no blood cells or a very sparse region of the slide 101) may have a high average intensity value, since the background would be bright. On the contrary, regions having more blood cells or a dense region may have a low average intensity value, since foreground is darker than the background. The average intensity value may be used as an indicator to estimate sparsity of the blood cells in the FOV.

Predefined QI threshold limit: Since a low average intensity value indicates a dense region, or a region with more visible blood cells, an upper limit may be defined for the average intensity value to accept an image as belonging to a monolayer region 143.

Density value: Density may be defined as ratio of the foreground area (i.e. the area comprising blood cells), to the total area in the FOV. To compute the foreground area, the QI determining module 235 may first apply Otsu's threshold on the green channel of the image. Number of pixels in the foreground corresponding to the Otsu's threshold is taken as the foreground area.

Predefined QI threshold limit: The ratio of foreground area to the total area is a rough indicator of the number of blood cells present in the image. A low value of density indicates very few blood cells. Thus, a lower threshold may be set on the density value. A high density value can indicate clumped cells, but that scenario may be handled by the other QIs.

Cell Count Value/RBC count value: The QI determining module 235 may use the cell count value in combination with the density value to quantify number of RBCs in the FOV. The QI determining module 235 may compute the cell count value as the number of blood cells present in the foreground, having a size within range of sizes of the RBCs. In some embodiments, the range of sizes of the RBCs may be between 3 μm and 10 μm in diameter. The QI determining module 235 may determine the number of blood cells using standard connected components analysis technique with 8-connectivity.

Predefined QI threshold limit: For the image that has passed the predefined QI threshold limit of the density value, the cell count value will be high if the blood cells are well separated. On the contrary, if the blood cells are clumped, then majority of the blood cells would fall beyond the range of the sizes of the RBCs, and may not be counted. Therefore, the monolayer region 143 should have a relatively high RBC count, whereas as sparse region (feather edge region 145) or the clumped region (thick region 141) should have a lower RBC count than the monolayer region 143. Therefore, a low threshold limit may be set for the cell count value.

RBC count ratio: RBC count ratio is an extension of the cell count value, and may be quantified as the percentage of the blood cells in the foreground that are of the size of the RBC. The thick region 141 of the PBS generally have RBCs overlapping with each other, thereby leading to the blood cells having larger size than the size of the RBC. Therefore, an image from the thick region 141 may have a lower value of RBC count ratio.

Predefined QI threshold limit: For the thick region 141 with a high number of blood cells, sufficient well separated RBCs to satisfy the predefined QI threshold limit of the cell count value may be present. However, the majority of the blood cells would still be clumped, and thus the image may not be an acceptable image. In such scenarios, the image can have a high RBC count, but would still have a low RBC count ratio. Therefore, a lower limit is set on the RBC count ratio.

Normalized sharpness value: The QI determining module 235 may determine the normalized sharpness value using the below Equation 1.

$$\text{Normalized Sharpness value} = S^*(1-D) \qquad \text{Equation 1}$$

In the above Equation 1,

S indicates sharpness value; and

D indicates density value.

In cases where the cell count value is low, the sharpness and density both tend to be proportionally low, hence normalized sharpness value is computed as a variant of the sharpness value.

Predefined QI threshold limit: A lower limit is set on the normalized sharpness.

In some embodiments, the QI determining module 235 may select predefined number of non-overlapping regions in each focused image. As an example, the predefined number of non-overlapping regions may be 5. The QI determining module 235 may determine the QIs in each of the predefined number of non-overlapping regions in each focused image. When the QIs of at least more than half of the predefined number of non-overlapping regions satisfy the predefined QI threshold limits, the QI determining module 235 may confirm that the position corresponding to the focused image belongs to the monolayer region 143. As an example, when QIs of at least 3 regions out of the 5 non-overlapping regions satisfy the predefined QI threshold limits, the position corresponding to the focused image is said to be belonging to the monolayer region 143. The QI determining module 235 may identify a stretch of the plurality of positions in the PBS 102 corresponding to the focused images whose QIs satisfied the predefined QI threshold limits, as the monolayer region 143.

In some embodiments, the QI determining module 235 may store the following tuple for each focused image captured at each of the plurality of positions in the QI data 211.

($X_i$, $Y_i$, $Z_i$, $f_i$, $S_i$, $I_i$, $Q_i$), wherein i denotes a position value in terms of 1 . . . N In the above tuple, $X_i$, indicates X co-ordinate of the $i^{th}$ position;

$Y_i$, indicates Y co-ordinate of the $i^{th}$ position;

$Z_i$, indicates Z co-ordinate of the $i^{th}$ position at which the sharpest focus was attained;

$f_i$, indicates a FOV flag that indicates whether the FOV of the focused image belongs to the monolayer region. In some embodiments, $f_i$, =1 may denote "Yes" the FOV belongs to the monolayer region and $f_i = 0$ may denote "No" the FOV does not belong to the monolayer region;

$S_i$, indicates maximum sharpness value at the $i^{th}$ position;

$I_i$, indicates average intensity value at the $i^{th}$ position; and $Q_i$ indicates a sub-tuple comprising the determined QIs at the $i^{th}$ position.

Further, the QI determining module 235 may construct a table comprising $S_i$ and $I_i$ of the plurality of positions and store the table in the QI data 211.

Further, the area determining module 237 may determine an area to be scanned in the monolayer region 143. In some embodiments, the area determining module 237 may determine an initiation point in the monolayer region 143 based on the cell count value determined in the focused image captured at each of the plurality of positions located in the monolayer region 143 and co-ordinates of each of the plurality of positions located in the monolayer region 143. In some embodiments, determining the initiation point may include determining a weighted average of "Y" co-ordinate value of each of the plurality of positions present in the monolayer region 143 using the below Equation 2.

$$\text{Initiation point} = \frac{\sum_i (w_i Y_i)}{\sum_i w_i} \qquad \text{Equation 2}$$

In the above Equation 2, $w_i$ indicates the cell count value at the $i^{th}$ position; and $Y_i$ indicates "Y" co-ordinate value at the $i^{th}$ position.

Further, the area determining module 237 may determine the area to be scanned in the monolayer region 143 based on the initiation point and a predefined scan pattern. To determine the area to be scanned, initially, the area determining module 237 may select the predefined scan pattern for scanning the area. As an example, the predefined scan pattern may include, but not limited to, a spiral scan pattern and a columnar scan pattern. The FIG. 2E (a) indicates the spiral scan pattern and the FIG. 2E (b) indicates the columnar scan pattern. Further, starting from the initiation point, the area determining module 237 may define a plurality of X-Y positions along the predefined scan pattern. In some embodiments, area covered by the plurality of X-Y positions along the predefined scan pattern in the monolayer region 143, may be determined as the area to be scanned. In some embodiments, the area to be scanned determined by the area determining module 237 may be an optimum area in the monolayer region 143 for achieving accurate results.

The area determining module 237 may store the initiation point, the plurality of X-Y positions and the determined area to be scanned as the scannable area data 213.

Further, the scanning module 239 may scan the area, starting from the initiation point in the predefined scan pattern. An exemplary initiation point 240 is shown in the FIG. 2E (a) and the FIG. 2E (b). In some embodiments, scanning the area may include traversing the plurality of X-Y positions defined along the predefined scan pattern and obtaining an image of sharpest focus at each of the traversed X-Y positions. Therefore, to obtain the image of sharpest focus at each of the traversed X-Y positions, the scanning module 239 may initially perform full z-stack focusing technique at the initiation point, starting from the homing Z position, until the sharpest focus is attained. Further, the scanning module 239 may capture an image corresponding to the sharpest focus that satisfies each of the predefined QI threshold limits. In some embodiments, if the FOV of the initiation point is empty, the scanning module 239 may proceed to the next X-Y position and again perform full z-stack focusing, until an image corresponding to the sharpest focus that satisfies each of the predefined QI threshold limits is obtained.

Further, the scanning module 239 may perform an iterative curve based focusing for each subsequent position (X-Y position) along the predefined scan pattern. For the current position, a Z co-ordinate corresponding to the sharpest focus in the previous position is considered as a first Z co-ordinate for the current position. Therefore, the scanning module 239 may not begin from the homing Z position for the subsequent positions. Upon determining the first Z co-ordinate for the current position, the scanning module 239 may identify the bell-curve graph matching the average intensity value and the sharpness value determined at the current position. Further, the scanning module 239 may determine a direction for moving along the Z-axis from the first Z co-ordinate.

In some embodiments, the scanning module 239 may select the direction for moving along the Z-axis based on two conditions:

If only one previous Z co-ordinate corresponding to the sharpest focus is determined, then the scanning module 239 may determine the direction of the movement to be upward (i.e. Z co-ordinate value is increased).

Consider Z co-ordinates corresponding to the sharpest focus of two FOVs, $Z_1$ and $Z_2$ are determined, wherein $Z_1$ corresponds to the most recent FOV. In such scenarios, the direction of the movement along the Z-axis is determined to be upward when $Z_1 > Z_2$. On the contrary, if $Z_2 > Z_1$, then the direction of the movement along the Z-axis is determined to be downward.

Upon selecting the direction of the movement, the scanning module 239 may determine step size of the focus steps for the movement along Z-axis, based on adaptive step-size technique. Since, the bell-curve graph corresponding to the current position is already identified, the scanning module 239 would infer that the sharpest focus corresponding to the current position may be proximal to peak of the identified bell-curve graph. Therefore, the scanning module 239 may determine the step size of the focus steps based on the peak of the identified bell-curve graph and width of the identified bell-curve graph. In some embodiments, when the width of the bell-curve graph is broad, the step size may be large. In some embodiments, when the width of the bell-curve graph is narrow, the step size may be small.

Upon determining the step size of the focus steps, the scanning module 239 may move two steps of the determined step size, along the selected direction and check for the following conditions:

If the sharpness value increases in at least one step, the scanning module 239 may continue along the same direction.

If the sharpness value increases at one step and decreases at another step, the scanning module 239 may still continue along the same direction, by inferring that the sharpness value may have decreased due to occurrence of noise.

If the sharpness value decreases at each of the two steps, the scanning module 239 may reverse the direction of the movement along Z-axis, from the selected direction, by inferring that the peak of the bell-curve graph has been crossed.

In some embodiments, even upon reversing the direction of the movement along Z-axis, if the sharpness value does not increase in either directions, the scanning module 239 may have focused an empty region that does not comprise any blood cells. Alternatively, the sharpness value may not increase in either directions when the scanning module 239 focuses at a region comprising a sudden steep variation in thickness of the slide 101. The scanning module 239 may confirm the occurrence of the first case, (i.e. focusing an empty region), when the average intensity of the FOV is higher than the predefined QI threshold limit, and may move to a new FOV. The scanning module 239 may confirm the occurrence of the second case, (i.e. sudden steep variation in thickness), when the average intensity of the FOV is below the predefined QI threshold limit, and may refocus the FOV by performing full z-stack focusing technique.

Further, the scanning module 239 may increase the focus steps based on the determined step-size in the decided direction. At one position, the scanning module 239 may detect that the sharpness value decreased from the sharpness value at previous Z position. In such scenarios, the scanning module 239 may perform a predefined technique such as binary search between the previous Z position and the current Z position to locate the sharpest focus of the current X-Y position. The scanning module 239 may capture the image corresponding to the sharpest focus and move to the subsequent X-Y position along the predefined scan pattern.

In some embodiments, the scanning module 239 may continue to scan the area until at least one of, exhaustion of the area or desired number of FOVs in the area that satisfy analysis criteria of the PBS 102 are attained. In some embodiments, the desired number of FOVs may be user defined. As an example, optimal number of FOVs to be captured may be 120 and minimum number of FOVs to be captured may be 80. However, maximum number of FOVs to be captured, may vary based on requirement of user. The images captured by the image capturing device 103 in the area to be scanned, may be stored as the scanned image data 215.

In some embodiments, while reversing direction of the slide stage 123, the slide stage 123 may not travel to a requested Z position due to backlash. Backlash values have been analysed and pre-generated by experimentation for a range of possible step sizes. While reversing direction of the slide stage 123, the processor 109 may estimate a backlash offset and add the backlash offset to the requested Z position, thereby achieving the required movement.

FIG. 3 shows a flowchart illustrating a method of determining an area to be scanned in a Peripheral Blood Smear (PBS) for analysis in accordance with some embodiments of the present disclosure.

As illustrated in FIG. 3, the method 300 includes one or more blocks illustrating a method of determining an area to be scanned in a Peripheral Blood Smear (PBS 102) for analysis. The method 300 may be described in the general context of computer executable instructions. Generally, computer executable instructions can include routines, programs, objects, components, data structures, procedures, modules, and functions, which perform functions or implement abstract data types.

The order in which the method 300 is described is not intended to be construed as a limitation, and any number of the described method blocks can be combined in any order to implement the method 300. Additionally, individual blocks may be deleted from the methods without departing from the spirit and scope of the subject matter described herein. Furthermore, the method 300 can be implemented in any suitable hardware, software, firmware, or combination thereof.

At block 301, the method 300 may include capturing, by a processor 109 of the PBS analyzing system 107, a focused image at each of plurality of positions in the PBS 102. In some embodiments, each of the plurality of positions may be marked from a predefined reference point and separate by a predefined distance.

At block 303, the method 300 may include determining, by the processor 109, Quality Indicators (QIs) in the focused image. The QIs may include, but not limited to, a cell count value, a normalized sharpness value, an average intensity value, a sharpness value, a density value and Red Blood Cells (RBC) count ratio. In some embodiments, the processor 109 may determine the QIs in predefined number of non-overlapping regions selected in the focused image.

At block 305, the method 300 may include, identifying, by the processor 109 a region in the PBS 102 where the QIs of the focused image satisfy predefined QI threshold limits, as a monolayer region 143 of the PBS 102.

At block 307, the method 300 may include, determining, by the processor 109, the initiation point in the monolayer region 143 based on the cell count value determined in the focused image captured at each of the plurality of positions located in the monolayer region 143 and co-ordinates of each of the plurality of positions located in the monolayer region 143.

At block 309, the method 300 may include, determining, by the processor 109, the area to be scanned in the monolayer region 143. In some embodiments, the processor 109 may determine the area to be scanned based on the initiation point and a predefined scan pattern selected by the processor 109 to scan the area. Further, upon determining the area to be scanned, the processor 109 may scan the area, starting from the initiation point, in the predefined scan pattern.

FIG. 4 is a block diagram of an exemplary computer system for implementing embodiments consistent with the present disclosure.

In some embodiments, FIG. 4 illustrates a block diagram of an exemplary computer system 400 for implementing embodiments consistent with the present invention. In some embodiments, the computer system 400 can be Peripheral Blood Smear (PBS) analyzing system 107 that is used for determining an area to be scanned in a PBS 102 for analysis. The computer system 400 may include a central processing unit ("CPU" or "processor") 402. The processor 402 may include at least one data processor for executing program components for executing user or system-generated business processes. The processor 402 may include specialized processing units such as integrated system (bus) controllers, memory management control units, floating point units, graphics processing units, digital signal processing units, etc.

The processor 402 may be disposed in communication with input devices 411 and output devices 412 via I/O interface 401. The I/O interface 401 may employ communication protocols/methods such as, without limitation, audio, analog, digital, stereo, IEEE-1394, serial bus, Universal Serial Bus (USB), infrared, PS/2, BNC, coaxial, component, composite, Digital Visual Interface (DVI), high-definition multimedia interface (HDMI), Radio Frequency (RF) antennas, S-Video, Video Graphics Array (VGA), IEEE 802.n /b/g/n/x, BLUETOOTH®, cellular (e.g., Code-Division Multiple Access (CDMA), High-Speed Packet Access (HSPA+), Global System For Mobile Communications (GSM), Long-Term Evolution (LTE), WiMax, or the like), etc.

Using the I/O interface 401, computer system 400 may communicate with input devices 411 and output devices 412.

In some embodiments, the processor 402 may be disposed in communication with a communication network 409 via a network interface 403. The network interface 403 may communicate with the communication network 409. The network interface 403 may employ connection protocols including, without limitation, direct connect, Ethernet (e.g., twisted pair 10/100/1000 Base T), Transmission Control Protocol/Internet Protocol (TCP/IP), token ring, IEEE 802.11a/b/g/n/x, etc. Using the network interface 403 and the communication network 409, the computer system 400 may communicate with an image capturing device 410 such as a camera, a smart phone, a tablet and the like. The communication network 409 can be implemented as one of the different types of networks, such as intranet or Local Area Network (LAN), Closed Area Network (CAN) and the like. The communication network 409 may either be a dedicated network or a shared network, which represents an association of the different types of networks that use a variety of protocols, for example, Hypertext Transfer Protocol (HTTP), CAN Protocol, Transmission Control Protocol/Internet Protocol (TCP/IP), Wireless Application Protocol (WAP), etc., to communicate with each other. Further, the communication network 409 may include a variety of network devices, including routers, bridges, servers, computing devices, storage devices, etc. In some embodiments, the processor 402 may be disposed in communication with a memory 405 (e.g., RAM, ROM, etc. not shown in FIG. 4) via a storage interface 404. The storage interface 404 may connect to memory 405 including, without limitation, memory drives, removable disc drives, etc., employing connection protocols such as Serial Advanced Technology Attachment (SATA), Integrated Drive Electronics (IDE), IEEE-1394, Universal Serial Bus (USB), fibre channel, Small Computer Systems Interface (SCSI), etc. The memory drives may further include a drum, magnetic disc drive, magneto-optical drive, optical drive, Redundant Array of Independent Discs (RAID), solid-state memory devices, solid-state drives, etc.

The memory 405 may store a collection of program or database components, including, without limitation, a user interface 406, an operating system 407, a web browser 408 etc. In some embodiments, the computer system 400 may store user/application data, such as the data, variables, records, etc. as described in this invention. Such databases may be implemented as fault-tolerant, relational, scalable, secure databases such as Oracle or Sybase.

The operating system 407 may facilitate resource management and operation of the computer system 400. Examples of operating systems include, without limitation, APPLE® MACINTOSH® OS X®, UNIX®, UNIX-like system distributions (E.G., BERKELEY SOFTWARE DISTRIBUTION® (BSD), FREEBSD®, NETBSD®, OPENBSD, etc.), LINUX® DISTRIBUTIONS (E.G., RED HAT®, UBUNTU®, KUBUNTU®, etc.), IBM® OS/2®, MICROSOFT® WINDOWS® (XP®, VISTA®/7/8, 10 etc.), APPLE® IOS®, GOOGLE™ ANDROID™, BLACKBERRY® OS, or the like. The User interface 406 may facilitate display, execution, interaction, manipulation, or operation of program components through textual or graphical facilities. For example, user interfaces may provide computer interaction interface elements on a display system operatively connected to the computer system 400, such as cursors, icons, check boxes, menus, scrollers, windows, widgets, etc.

In some embodiments, the computer system 400 may implement the web browser 408 stored program components. The web browser 408 may be a hypertext viewing application, such as MICROSOFT® INTERNET EXPLORER®, GOOGLE™ CHROME", MOZILLA® FIREFOX®, APPLE® SAFARI®, etc. Secure web browsing may be provided using Secure Hypertext Transport Protocol (HTTPS), Secure Sockets Layer (SSL), Transport Layer Security (TLS), etc. Web browsers 408 may utilize facilities such as AJAX, DHTML, ADOBE® FLASH®, JAVASCRIPT®, JAVA®, Application Programming Interfaces (APIs), etc.

Furthermore, one or more computer-readable storage media may be utilized in implementing embodiments consistent with the present invention. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, (i.e., non-transitory). Examples include Random Access Memory (RAM), Read-Only Memory (ROM), volatile memory, non-volatile memory, hard drives, Compact Disc (CD) ROMs, Digital Video Disc (DVDs), flash drives, disks, and any other known physical storage media.

Advantages of the Embodiment of the Present Disclosure are Illustrated Herein.

The present disclosure provides a method and a system for determining an area to be scanned in a Peripheral Blood Smear (PBS) for analysis.

The present disclosure determines an area to be scanned within a monolayer region of the PBS, that yields accurate and fast results.

The present disclosure discloses a feature wherein a single high magnification lens is used to identify the area to be scanned and for further scanning the area, thereby reducing enormous amount of time that is spent by the existing techniques in performing a two stage scanning process for locating the objects using low magnification lens and analyzing the located objects of interest using the high magnification lens.

The present disclosure provides a feature wherein first Z position for every subsequent X-Y position while scanning the area would be considered as a Z position corresponding to sharpest focus of a previous position, instead of starting from a homing Z position. This feature helps in reducing the scanning time by helping in achieving images of sharpest focus at a faster rate.

A description of an embodiment with several components in communication with each other does not imply that all such components are required. On the contrary a variety of optional components are described to illustrate the wide variety of possible embodiments of the invention. When a single device or article is described herein, it will be apparent that more than one device/article (whether or not they cooperate) may be used in place of a single device/article. Similarly, where more than one device or article is described herein (whether or not they cooperate), it will be apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The specification has described a method and a system for determining an area to be scanned in a Peripheral Blood Smear (PBS) for analysis. The illustrated steps are set out to explain the exemplary embodiments shown, and it should be anticipated that on-going technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open-ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the embodiments of the present invention are intended to be illustrative, but not limiting, of the scope of the invention, which is set forth in the following claims.

REFERRAL NUMERALS

| Reference Number | Description |
|---|---|
| 100 | Architecture |
| 101 | Slide |
| 102 | Peripheral Blood Smear (PBS) |
| 103 | Image capturing device |
| 107 | Peripheral Blood Smear (PBS) analysing system |
| 109 | Processor |
| 111 | I/O interface |
| 113 | Memory |
| 120 | Automatic slide scanner |
| 123 | Slide stage |
| 125 | X-axis mechanism |
| 127 | Y-axis mechanism |
| 129 | Z-axis mechanism |
| 131 | Optics module |
| 132 | Illumination unit |
| 133 | Motherboard |
| 135 | Camera module |
| 141 | Thick region |
| 143 | Monolayer region |
| 145 | Feather edge region |

-continued

| Reference Number | Description |
|---|---|
| 203 | Data |
| 205 | Modules |
| 207 | Focus data |
| 209 | Graph data |
| 211 | Quality Indicator (QI) data |
| 213 | Scannable area data |
| 215 | Scanned image data |
| 219 | Other data |
| 231 | Focusing module |
| 232a | Homing Z position |
| 232b | Focus distance of high magnification lens |
| 232c | Exemplary predefined reference point |
| 232d | Exemplary plurality of positions |
| 233 | Graph plotting module |
| 235 | Quality Indicator (QI) determining module |
| 237 | Area determining module |
| 239 | Scanning module |
| 240 | Exemplary initiation point |
| 241 | Other modules |
| 400 | Exemplary computer system |
| 401 | I/O Interface of the exemplary computer system |
| 402 | Processor of the exemplary computer system |
| 403 | Network interface |
| 404 | Storage interface |
| 405 | Memory of the exemplary computer system |
| 406 | User interface |
| 407 | Operating system |
| 408 | Web browser |
| 409 | Communication network |
| 410 | Image capturing device of the exemplary computing system |
| 411 | Input devices |
| 412 | Output devices |

The invention claimed is:

1. A method for determining an area to be scanned in a Peripheral Blood Smear (PBS) for analysis, the method comprising:
capturing, by a PBS analysing system, a focused image at each of a plurality of positions in the PBS, wherein the plurality of positions are selected along a horizontal line of axis that extends across length of the PBS starting from a predefined reference point;
determining, by the PBS analysing system, Quality Indicators (QIs) in the focused image captured at each of the plurality of positions, wherein the QIs comprise a cell count value, a normalized sharpness value and an average intensity value;
identifying, by the PBS analysing system, a region in the PBS where the QIs of the focused image satisfy predefined QI threshold limits, as a monolayer region of the PBS; and
determining, by the PBS analysing system, an initiation point in the monolayer region based on the cell count value determined in the focused image captured at each of the plurality of positions located in the monolayer region and co-ordinates of each of the plurality of positions located in the monolayer region; and
determining, by the PBS analysing system, the area to be scanned in the monolayer region based on the initiation point and a predefined scan pattern selected for scanning the area.

2. The method as claimed in claim 1, wherein each of the plurality of positions are marked on the PBS from the predefined reference point.

3. The method as claimed in claim 2, wherein each of the plurality of positions marked from the predefined reference point are separated by a predefined distance until end of the PBS.

4. The method as claimed in claim 1, wherein the QIs further comprises a sharpness value, a density value and Red Blood Cells (RBC) count ratio.

5. The method as claimed in claim 1 further comprises a Field Of View (FOV) flag associated with each of the plurality of positions that indicates whether FOV corresponding to each of the plurality of positions belongs to the monolayer region.

6. The method as claimed in claim 1, wherein the focused image is captured at each of the plurality of positions using an image capturing device associated with the PBS analysing system.

7. The method as claimed in claim 1, wherein the QIs are determined in predefined number of non-overlapping regions selected in the focused image, wherein the QIs confirm the monolayer region when the QIs of at least more than half of the predefined number of non-overlapping regions satisfy the predefined QI threshold limits.

8. The method as claimed in claim 1, wherein determining the initiation point comprises computing, by the PBS analysing system, a weighted average of "Y" co-ordinate value of each of the plurality of positions present in the monolayer region using a predefined equation mentioned below:

$$\text{Initiation Point} = \frac{\sum_i (w_i Y_i)}{\sum_i w_i}$$

wherein, $w_i$ indicates cell count value and $Y_i$ indicates "Y" co-ordinate value.

9. The method as claimed in claim 1 further comprises plotting, by the PBS analysing system, a bell-curve graph indicating focus steps at each of the plurality of positions and corresponding sharpness at each focus step of the plurality of positions, when the focused image is captured.

10. The method as claimed in claim 1 further comprises scanning, by the PBS analysing system, the area in the predefined scan pattern around the initiation point in the area.

11. The method as claimed in claim 10, wherein the predefined scan pattern comprises at least one of a spiral scan pattern and a columnar scan pattern.

12. The method as claimed in claim 10, wherein the scanning is continued until exhaustion of the area.

13. The method as claimed in claim 10, wherein the scanning is continued until desired number of Field Of Views (FOVs) in the area that satisfy analysis criteria of the PBS are attained.

14. A Peripheral Blood Smear (PBS) analysing system for determining an area to be scanned in a PBS for analysis, the PBS analysing system comprising:
a processor; and
a memory communicatively coupled to the processor, wherein the memory stores the processor executable instructions, which, on execution, causes the processor to:
capture a focused image at each of a plurality of positions in the PBS, wherein the plurality of positions are selected along a horizontal line of axis that extends across length of the PBS starting from a predefined reference point;
determine Quality Indicators (QIs) in the focused image captured at each of the plurality of positions, wherein the QIs comprise a cell count value, a normalized sharpness value and an average intensity value;
identify a region in the PBS where the QIs of the focused image satisfy predefined QI threshold limits, as a monolayer region of the PBS;
determine an initiation point in the monolayer region based on the cell count value determined in the focused image captured at each of the plurality of positions located in the monolayer region and co-ordinates of each of the plurality of positions located in the monolayer region; and
determine the area to be scanned in the monolayer region based on the initiation point and a predefined scan pattern selected for scanning the area.

15. The PBS analysing system as claimed in claim 14, wherein the processor marks each of the plurality of positions on the PBS from the predefined reference point.

16. The PBS analysing system as claimed in claim 15, wherein each of the plurality of positions marked from the predefined reference point are separated by a predefined distance until end of the PBS.

17. The PBS analysing system as claimed in claim 14, wherein the QIs further comprises a sharpness value, a density value and Red Blood Cells (RBC) count ratio.

18. The PBS analysing system as claimed in claim 14 further comprises a Field Of View (FOV) flag associated with each of the plurality of positions that indicates whether FOV corresponding to each of the plurality of positions belongs to the monolayer region.

19. The PBS analysing system as claimed in claim 14, wherein the processor captures the focused image at each of the plurality of positions using an image capturing device associated with the PBS analysing system.

20. The PBS analysing system as claimed in claim 14, wherein the processor determines the QIs in predefined number of non-overlapping regions selected in the focused image, wherein the QIs confirm the monolayer region when the QIs of at least more than half of the predefined number of non-overlapping regions satisfy the predefined QI threshold limits.

21. The PBS analysing system as claimed in claim 14, wherein to determine the initiation point, the processor is configured to compute a weighted average of "Y" co-ordinate value of each of the plurality of positions present in the monolayer region using a predefined equation mentioned below:

$$\text{Initiation point} = \frac{\sum_i (w_i Y_i)}{\sum_i w_i}$$

wherein, $w_i$ indicates cell count value and $Y_i$ indicates "Y" co-ordinate value.

22. The PBS analysing system as claimed in claim 14, wherein the processor is further configured to plot a bell-curve graph indicating focus steps at each of the plurality of positions and corresponding sharpness at each focus step of the plurality of positions, when the focused image is captured.

23. The PBS analysing system as claimed in claim 14, wherein the processor is further configured to scan the area in the predefined scan pattern around the initiation point in the area.

24. The PBS analysing system as claimed in claim 23, wherein the predefined scan pattern comprises at least one of a spiral scan pattern and a columnar scan pattern.

25. The PBS analysing system as claimed in claim 23, wherein the processor continues scanning until exhaustion of the area.

26. The PBS analysing system as claimed in claim 23, wherein the processor continues scanning until desired number of Field Of Views (FOVs) in the area that satisfy analysis criteria of the PBS are attained.

* * * * *